United States Patent
Molloy et al.

(10) Patent No.: US 6,332,363 B1
(45) Date of Patent: Dec. 25, 2001

(54) BIOSENSOR, METHOD OF FORMING AND USE

(75) Inventors: James Oscar Molloy, Suffolk; Colin Hugh Maule, Cambridge, both of (GB)

(73) Assignee: Thermo FAST UK Limited (GB)

( * ) Notice: Subject to any disclaimer, the term of this patent is extended or adjusted under 35 U.S.C. 154(b) by 0 days.

(21) Appl. No.: 09/254,096

(22) PCT Filed: Sep. 2, 1997

(86) PCT No.: PCT/GB97/02347

§ 371 Date: Oct. 15, 1999

§ 102(e) Date: Oct. 15, 1999

(87) PCT Pub. No.: WO98/10288

PCT Pub. Date: Mar. 12, 1998

(30) Foreign Application Priority Data

Sep. 6, 1996 (GB) .................................................. 9618635

(51) Int. Cl.[7] .................................................. G01B 7/16
(52) U.S. Cl. .............................. 73/776; 427/577
(58) Field of Search .................................. 73/19.03, 763, 73/774, 776; 310/313; 427/577

(56) References Cited

U.S. PATENT DOCUMENTS

| | | | |
|---|---|---|---|
| 5,273,788 | * 12/1993 | Yu ........................................ | 427/554 |
| 5,695,832 | * 12/1997 | Hirano et al. ........................ | 427/577 |
| 5,880,552 | * 3/1999 | McGill et al. ....................... | 310/313 R |

FOREIGN PATENT DOCUMENTS

92/03720 * 3/1992 (WO) .
93/24828 * 12/1993 (WO) .

* cited by examiner

*Primary Examiner*—Max Noori
(74) *Attorney, Agent, or Firm*—Nixon Peabody LLP

(57) ABSTRACT

A sensor device (1–5) has a sensing surface on which, in use, first molecules (5) are immobilized. The first molecules (5) are capable of interaction with second molecules which may be present in a sample of fluid applied to the sensing surface, such interaction resulting in a measurable change of some physical property of the sensor device. The sensing surface is coated with a layer (4) of diamond-like carbon to protect and preserve the integrity of the sensing surface.

19 Claims, 2 Drawing Sheets

BIOSENSOR, METHOD OF FORMING AND USE

Figure 1:
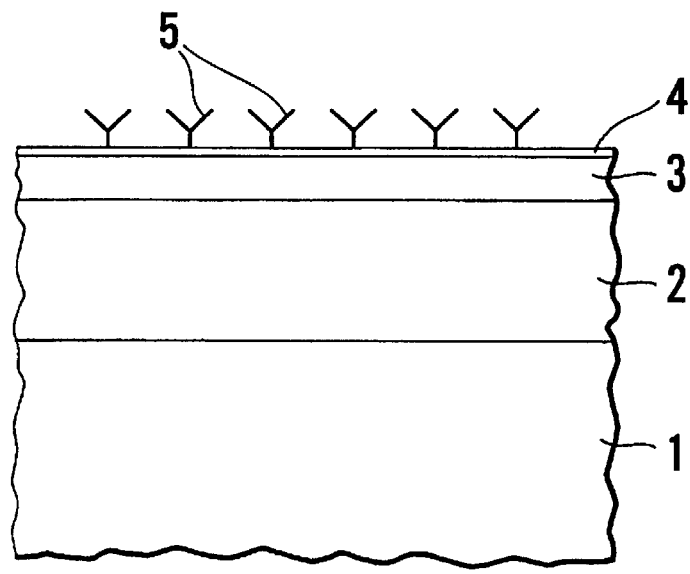

This invention relates to improvements in or relating to sensors, and in particular to those sensors termed biosensors, ie devices for the analysis and investigation of biological or biologically active species such as antigens and antibodies, enzymes, substrates, proteins, haptens, whole cells and cellular fragments and nucleic acids.

Many devices for the automatic determination of biochemical analytes in solution have been proposed in recent years. Typically, such devices (biosensors) include a sensitised coating layer which is located in the evanescent region of a resonant field. Typically, the coating layer comprises a layer of biological molecules chemically linked to the surface, either directly or via an intermediate linking molecule, or immobilised within a matrix of, for instance, hydrogel molecules bound to the surface.

Detection of the molecule under investigation ("the analyte") typically utilizes optical techniques such as, for example, surface plasmon resonance (SPR) or frustrated total reflection (FTR), and is based on changes in the thickness and/or refractive index of the coating layer resulting from interaction of that layer with the analyte. This causes a change in the properties of the sensor, eg a change in the angular position of the resonance. Other forms of biosensor include devices with semiconducting surfaces, the electrical properties of the device being monitored and, notably, acoustic devices in which changes in surface bulk loading are detected.

Since the measurements made using biosensors of the types described are essentially measurements of events or changes occurring at the sensitised surface of the device, it is critical to the accuracy and reliability of the measurements that the integrity of that surface is maintained. In an SPR or FTR sensor, for example, the device monitors the resonating properties of a structure the natural frequency of which is altered as changes take place at its surface. If the sample can alter the bulk of the structure in a non-specific manner then the integrity of the measurement is destroyed. In practice, maintenance of surface integrity may not be achieved and this gives rise to errors in the experimental results and/or greatly limits the useful life of the sensor devices. For example, repeated application of reagents to the surface (as is inevitable in a series of measurements) may result in attrition of the surface, with a consequent unpredictable change in properties. The surface may be somewhat porous, with the result that reagents may be absorbed, again changing the properties of the device. Chemical linkages between the surface and the molecules immobilized on it may also become broken in the course of chemical treatment.

There has now been devised an improvement to sensors of the kind generally described above which overcomes or substantially mitigates the disadvantages of the prior art.

According to the invention, a sensor device has a sensing surface on which, in use, first molecules are immobilized, the first molecules being capable of interaction with second molecules which may be present in a sample of fluid applied to the sensing surface, such interaction resulting in a measurable change of some physical property of the sensor device, wherein the sensing surface is coated with a layer of diamond-like carbon.

The sensor device according to the invention is advantageous primarily in that the layer of diamond-like carbon (DLC) protects and preserves the integrity of the sensing surface. The device is impervious to the reagents and fluids with which it is, in use, contacted. Problems of attrition of the surface and porosity are reduced, and linkages of the first molecules to the surface are more stable. Furthermore, and particularly importantly, by appropriate control of the composition of the diamond-like carbon layer (as described below) a wide variety of functionalities may be incorporated into it in a thickness-dependent manner.

DLC is a dense, partially $sp^3$ bonded form of amorphous carbon. Its atomic structure consists of a network of $sp^3$ and $sp^2$ sites, the connectivity of the $sp^3$ sites controlling the mechanical properties of the material. DLC is conventionally used as a hard coating material, ie to confer "diamond-like" properties such as mechanical hardness and low friction on substrate materials. Since the purpose of the DLC layer used in the present invention is not primarily to confer a high degree of hardness on the active surface of the sensor device, the layer may have a hardness which is considerably less than that achieved in conventional applications of DLC.

The DLC layer may be formed by plasma deposition or chemical vapour deposition techniques. Typically, monomeric starting materials in the gas phase are introduced into a vacuum chamber containing a pair of electrodes. The device to be coated is supported in the chamber on one of the electrodes and a radiofrequency or microwave discharge is applied.

Generally, the starting material includes a hydrocarbon, most preferably methane. However, in principle any suitable hydrocarbon may be used, eg ethylene, acetylene, ethane, or aromatic species such as toluene and styrene. Mixtures of starting materials may be used to give desired physical properties.

It may also be desirable to incorporate other chemical functionality in the DLC layer. For instance, by introducing $CH_3NH_2$ gas in the final stages of the deposition, a DLC layer may be formed with a surface which includes amino groups. Such groups may be useful for the direct immobilization of biomolecules. Similarly, inclusion of carboxylate-containing species in the vapour may give rise to a surface with carboxylate functionality. The starting materials may also include small quantities of gases such as argon, neon, nitrogen, oxygen or helium. Appropriate combinations of starting materials may also be used to produce DLC layers having particularly hydrophobic or hydrophilic properties.

Because the polymerisation reaction is essentially simple, a high degree of control can be exercised over the chemical and physical nature of the DLC layer, enabling the properties of that layer to be easily tailored to the particular application for which the sensor device is intended. One physical parameter which is important is the density of the DLC layer, which is determined largely by the proportion of $sp^3$ to $sp^2$ hybridized carbon. For optical sensors, a dense DLC layer is desirable to minimise the thickness of the DLC layer necessary to provide the necessary degree of protection without adversely affecting the optical properties of the sensor. The density (and thickness) of the DLC layer may be less important, or not at all important, for non-optical sensors.

The DLC layer should have a thickness which is sufficient to confer the desired degree of protection on the sensing surface of the sensor device. The thickness of the DLC layer can be controlled by appropriate choice of the operating parameters of the deposition apparatus, notably the period for which the deposition is carried out. In general, the thickness should be no greater than the minimum required, so as to avoid any possible deleterious effects of the DLC layer on the properties, eg the sensitivity, of the sensor device. Typically, the DLC layer will have a thickness of less than 100 nm, more preferably less than 50 nm, and particularly less than 20 nm. A thickness of greater than 1 nm, and generally greater than 5 nm will normally be required. The thickness is most preferably of the order of 10 nm.

The DLC layer may be applied directly to the surface of the sensor device which it is desired to protect. However, since the DLC layer may not adhere sufficiently well to the material of that surface, it may be necessary to apply first a thin layer of another material to which the DLC layer will adhere well.

The sensor device according to the invention may be of any type, eg an optical sensor or any other formn of sensor in which changes at the sensing surface result in a measurable change of physical property. One preferred form of optical sensor is based on frustrated total reflection. The principles of frustrated total reflection (FTR) are well known; the technique is described, for example, by Bosacchi and Oehrle [Applied Optics (1982), 21, 2167–2173]. An FTR device for use in immunoassay is disclosed in European Patent Application No 0205236A and comprises a cavity layer bounded on one side by the sample under investigation and on the other side by a spacer layer which in turn is mounted on a substrate. The substrate-spacer layer interface is irradiated with monochromatic radiation such that total reflection occurs, the associated evanescent field penetrating through the spacer layer. If the thickness of the spacer layer is correct and the incident parallel wave vector matches one of the resonant mode propagation constants, the total reflection is frustrated and radiation is coupled into the cavity layer. The cavity layer must be composed of material which has a higher refractive index than the spacer layer and which is transparent at the wavelength of the incident radiation.

An FTR sensor will generally include an optical structure comprising
  a) a cavity layer of transparent dielectric material of refractive index $n_3$,
  b) a dielectric substrate of refractive index $n_1$, and
  c) interposed between the cavity layer and the substrate, a dielectric spacer layer of refractive index $n_2$.

In use, the interface between the substrate and the spacer layer is irradiated with light such that internal reflection occurs. Resonant propagation of a guided mode in the cavity layer will occur, for a given wavelength, at a particular angle of incidence of the exciting radiation.

The angular position of the resonant effect depends on various parameters of the sensor device, such as the refractive indices and thicknesses of the various layers. It is a pre-requisite that the refractive index $n_3$ of the cavity layer and the refractive index $n_1$, of the substrate should both exceed the refractive index $n_2$ of the spacer layer. Also, since at least one mode must exist in the cavity to achieve resonance, the cavity layer must exceed a certain minimum thickness.

The cavity layer is preferably a thin-film of dielectric material. Suitable materials for the cavity layer include silicon nitride, hafnium dioxide, zirconium dioxide, titanium dioxide, aluminum oxide and tantalum oxide.

The dielectric spacer layer must have a lower refractive index than both the cavity layer and the substrate. The layer may, for example, comprise an evaporated or sputtered layer of magnesium fluoride. In this case an infra-red light injection laser may be used as light source. The light from such a source typically has a wavelength around 600–800 nm. Other suitable materials include lithium fluoride and silicon dioxide.

The refractive index of the substrate ($n_1$) must be greater than that ($n_2$) of the spacer layer but the thickness of the substrate is generally not critical.

By contrast, the thickness of the cavity layer must be so chosen that resonance occurs within an appropriate range of coupling angles. The spacer layer will typically have a thickness of the order of several hundred nanometres, say from about 200 nm to 2000 nm, more preferably 500 to 1500 nm, eg 1000 mn. The cavity layer typically has a thickness of a few tens of nanometres, say 10 to 200 nm, more preferably 30 to 150 nm, eg 100 nm.

It is particularly preferred that the cavity layer has a thickness of 30 to 150 nm and comprises a material selected from silicon nitride, hafnium dioxide, zirconium dioxide, titanium dioxide, tantalum oxide and aluminum oxide, and the spacer layer has a thickness of 500 to 1500 nm and comprises a material selected from magnesium fluoride, lithium fluoride and silicon dioxide, the choice of materials being such that the refractive index of the spacer layer is less than that of the cavity layer.

Preferred materials for the cavity layer and the spacer layer are silicon nitride and silicon dioxide respectively.

At resonance, the incident light is coupled into the cavity layer by FTR, propagates a certain distance along the cavity layer, and couples back out (also by FTR). The propagation distance depends on the various device parameters but is typically of the order of 1 or 2 mm.

At resonance the reflected light will undergo a phase change, and it is this which may be detected. Alternatively, as described in International Patent Application No WO 92/03720 the cavity layer and/or spacer layer may absorb at resonance, resulting in a reduction in the intensity of the reflected light.

The DLC layer is preferably formed on the surface of the cavity layer after the spacer layer and cavity layer have been applied to the substrate. In addition to the DLC layer, the cavity layer or the cavity layer and the spacer layer may be formed by plasma deposition or chemical vapour deposition techniques. The substrate may, for example, be placed in the deposition chamber and the spacer layer, cavity layer and DLC layer formed sequentially.

Another particular form of sensor which may be mentioned is the type of optical sensor disclosed in copending International Patent Application WO 97/29362. Such a device comprises a substrate having a waveguide formed on at least part of the surface thereof, the waveguide having a first major surface which constitutes an interface between the waveguide and the substrate and a second major surface upon which the first molecules are immobilized, at least a region of the first and/or second major surface being formed with a periodic refractive index modulation. When such a device is modified in accordance with the present invention, the DLC layer is applied to the second major surface of the waveguide, ie between the waveguide and the first molecules.

With such a device, as described in WO 97/29362, high intensity of reflected light may be observed. Such high reflection may be termed "anomalous" or "abnormal" reflection. Interaction of the molecular species immobilized on the waveguide surface with analyte molecules in a sample which is contacted with the waveguide causes a local change in refractive index in the vicinity of the waveguide surface. This in turn changes the angle of incidence or wavelength at which the reflection maximum occurs, providing a sensitive indicator of the chemical interaction taking place at the surface.

The periodic refractive index modulation is preferably a surface relief profile or a grating formed in the surface of the substrate to which the waveguide coating is applied and/or in the surface of the waveguide on which the first molecules are immobilized. The periodic refractive index modulation may be formed in one or both major surfaces of the waveguide.

The grating may have a variety of forms. For example, it may be sinusoidal, rectangular, triangular (saw-tooth) or trapezoidal.

The substrate is conveniently a chip, eg of glass or silica, and, in use, the superstrate is most commonly an aqueous sample. The waveguide is preferably of relatively high refractive index, e.g. a material having a refractive index of, say, 1.80 to 2.50. Suitable materials for the waveguide include hafnium dioxide, silicon nitride, tantalum pentoxide and titanium oxide.

The optimal physical dimensions of the sensor device, grating etc will depend on the wavelength of the incident light. In the following description, the values given for the waveguide thickness, grating depth and period, light beam diameter etc encompass those suitable for commonly-used wavelengths, eg a wavelength of 633 nm.

Typically, the wa,.eguide may have a thickness of the order of 50 nm to 300 nm, more preferably 100 nm to 200 nm. We particularly prefer the thickness of the waveguide to be in the range 140 nm to 180 nm.

The depth of the periodic refractive index modulations (e.g. the corrugations in the surface of the substrate) is preferably less than 50 nm, more preferably less than 25 nm, eg typically 2 nm to 20 nm or 5 nm to 10 nm. The period of the grating is typically 300 nm to 1000 nm, more preferably 600 nm to 1000 nm.

For use in the analysis of biochemical species, the first molecules immobilized, in use, on the sensing surface of the sensor device (ie on the DLC layer) will generally be biomolecules, eg specific binding partners for the second molecules (the analyte). The first molecules may be bound to the surface by methods which are well known to those skilled in the art. The first molecules may be covalently bound to the DLC layer, either directly or via linking molecules, or may be bound to a matrix, eg a porous matrix of a hydrogel such as agarose or dextran, which is itself bound to the DLC layer. Examples of pairs of classes of molecules, one of which may be immobilized as first molecule for interaction with the other as second molecule are:

antigen/antibody hormone/hormone receptor polynucleotide strand/complementary strand avidin/biotin enzyme/substrate carbohydrate/lectin The sensor device may be used for the quantitative or qualitative determination of the second molecule in a sample applied to the sensing surface, or may be used to study the interaction of the second molecules with the immobilized first molecules.

Figure 2:
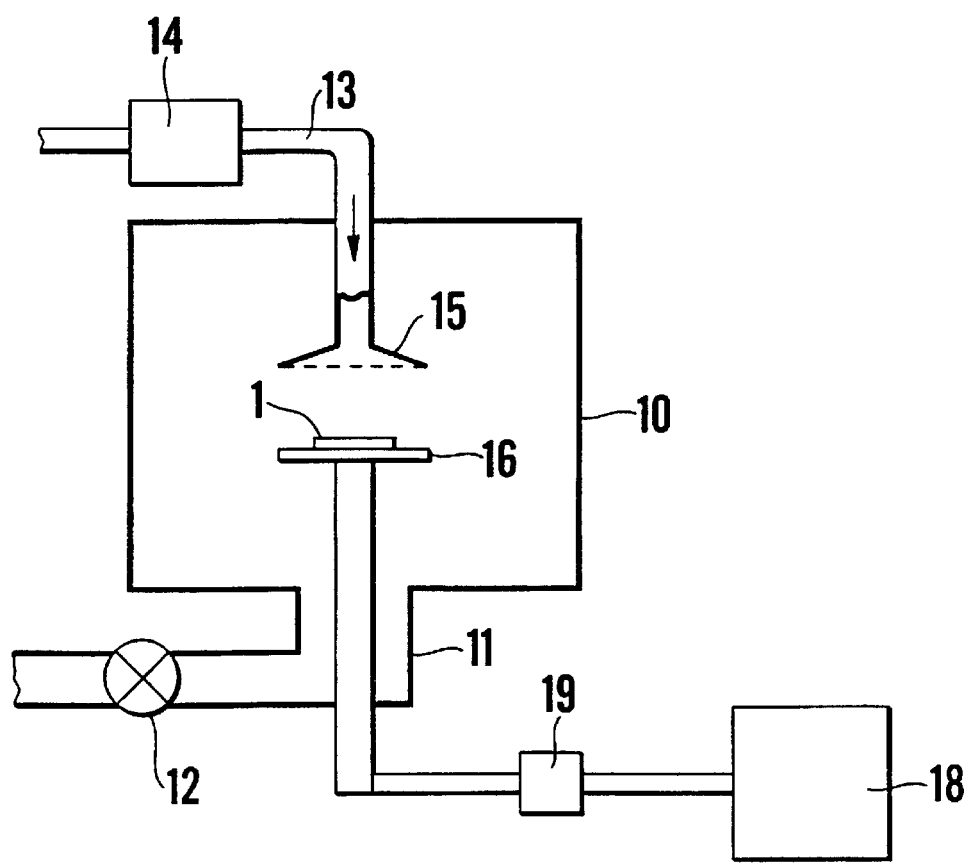
Figure 3:
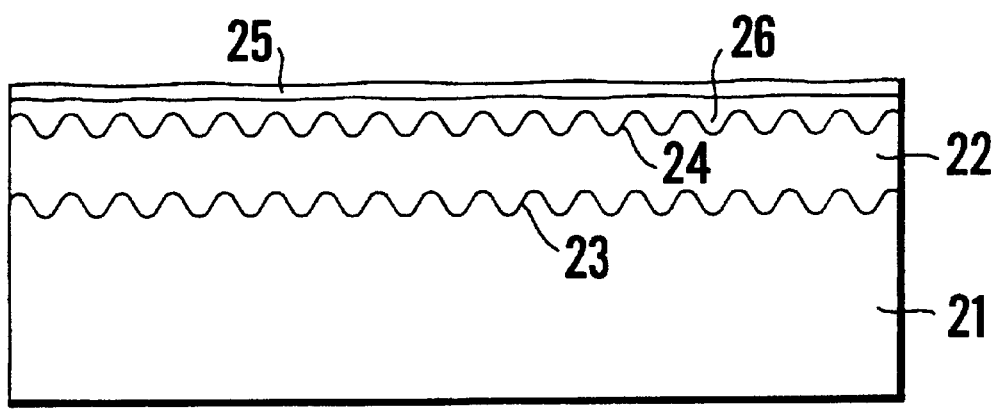

The invention will now be described in greater detail, by way of illustration only, with reference to the accompanying drawings, in which FIG. 1 is a schematic cross-sectional view of a first sensor device according to the invention;

FIG. 2 is a schematic view of chemical vapour deposition apparatus used in the manufacture of the sensor device of FIG. 1; and FIG. 3 is a schematic cross-sectional view of a second sensor device according to the invention.

Referring first to FIG. 1, a biosensor based on the principle of frustrated total reflection (FTR) comprises a substrate 1 in the form of a glass chip, on the surface of which are formed successively a spacer layer 2 of silicon oxide and a cavity layer 3 of silicon nitride. The spacer layer 2 has a thickness of approximately 700 nm and the cavity layer 3 a thickness of approximately 100 nm.

The surface of the cavity layer 3 is coated with a protective layer 4 of diamond-like carbon of approximate thickness 10 nm. Antibodies 5 are covalently bound to the surface of the protective layer 4.

FIG. 2 shows apparatus used for the deposition of the spacer layer 2, cavity layer 3 and protective layer 4 on the substrate 1. The apparatus comprises a vacuum chamber 10 with an exhaust port 11 formed in its base, the exhaust port 11 being connected to a pump 12. Gases are fed to the chamber 10 through an inlet conduit 13, via a mass flow controller 14. The inlet conduit 13 terminates in a "showerhead" arrangement 15 which constitutes a first electrode.

A support 16 is positioned below the shower-head 15 and constitutes a second electrode. The support is connected to a 13.65 MHz radiofrequency generator 18, via a matching unit 19.

In use, the substrate 1 is positioned on the support 16 and the sequence of layers 2,3,4 built up sequentially by chemical vapour deposition. A gas is passed through the showerhead 15 into the space between the shower-head 15 and the support 16. A plasma is formed in that space and deposition of ions created in the plasma takes place. First, the spacer layer 2 is formed by introduction of an appropriate precursor gas through the shower-head 15 and appropriate setting of operating parameters. The precursor gas and operating parameters are then changed to form the cavity layer 3. A further change of gas and operating parameters leads to formation of the protective layer 4, as described below.

In order to form the protective layer 4, methane gas is fed through the inlet conduit 13 as indicated by the arrow. The operating parameters which are used to control the extent and rate of deposition are principally the operating temperature, the flow rate of gas into the chamber 10, the pressure within the chamber 10 and the applied bias voltage. A typical set of parameters is:

| | |
|---|---|
| Temperature | room temperature |
| Flow rate | 10 sccm (standard cubic centimeters/minute) |
| Pressure | 50 mTorr |
| Self-generated Bias voltage | 70 V |

With these operating conditions, deposition of a protective layer 4 having a thickness of approximately 10 nm typically takes about 5 minutes.

The arrangement described above, in which the workpiece (the substrate 1) is placed on the driven electrode is unusual; a more conventional deposition arrangement being one in which the other electrode is driven.

Finally, FIG. 3 shows a second form of sensor device according to the invention. This device is of the type described in WO 97/29362 and comprises a substrate in the form of a chip 21 (eg of glass or silica) approximately 7 mm square and 2 mm in thickness. The chip 21 has a refractive index of 1.46. Coated on the upper surface of the chip 21 is a waveguide 22.

The interface between the chip 21 and the waveguide 22 is formed with a periodic relief profile or grating 23 (the grating 23 is shown as being sinusoidal though in practice it may be generally rectangular). The waveguide 22 is formed by deposition on the chip 21 and a corresponding relief profile 24 may thus be formed also on the upper surface of the waveguide 22. The upper surface of the waveguide 22 is coated with a protective layer 26 of diamond-like carbon of approximate thickness 10 nm (by a process similar to that described above in relation to the embodiment of FIG. 1). A layer 25 of biomolecules, eg antibodies, is immobilized on the protective layer 26 in a known manner.

What is claimed is:

1. A sensor device for detecting the binding of first molecules to second molecules, said sensor device comprising:

a sensor surface, said sensor surface having an impervious layer of diamond-like carbon (DLC) applied thereto, and said impervious layer having first molecules immobilized thereon, wherein contact of a sample containing said second molecules with said sensor device results in binding between said first molecules and said second molecules.

2. A sensor device according to claim 1, wherein the DLC layer is formed by a plasma deposition or chemical vapour deposition technique.

3. A sensor device according to claim 2, wherein in said technique monomeric starting materials in the gas phase are introduced into a vacuum chamber containing a pair of electrodes, a device to be coated being supported in the chamber on one of the electrodes, and a radiofrequency or microwave discharge is applied.

4. A sensor device as claimed in claim 3, wherein the starting material includes a hydrocarbon, most preferably methane.

5. A sensor device as claimed in claim 1, wherein the DLC layer has a surface which includes amino groups.

6. A sensor device as claimed in claim 1, wherein the DLC layer has a surface which includes carboxylate groups.

7. A sensor device as claimed in claim 1, wherein the DLC layer has a thickness of less than 100 nm.

8. A sensor device as claimed in claim 1, wherein the DLC layer has a thickness of greater than 1 nm.

9. A sensor device as claimed in claim 1, wherein the DLC layer has a thickness of the order of 10 nm.

10. A sensor device as claimed in claim 1, which is an optical sensor based on frustrated total reflection, and comprising a) a cavity layer of transparent dielectric material of refractive index $n_3$, b) a dielectric substrate of refractive index $n_1$, and c) interposed between the cavity layer and the substrate, a dielectric spacer layer of refractive index $n_2$.

11. A sensor device as claimed in claim 1, which is an optical sensor comprising a substrate having a waveguide formed on at least part of the surface thereof, the waveguide having a first major surface which constitutes an interface between the waveguide and the substrate and a second major surface upon which the DLC layer is applied, at least a region of the first and/or second major surface being formed with a periodic refractive index modulation.

12. A method for the analysis of biochemical species in a fluid, which method comprises contacting a sample of the fluid with molecules immobilized on the DLC layer of a sensor as claimed in claim 1.

13. A method of forming a sensor as claimed in claim 1, which method comprises supporting said sensor device on one of a pair of electrodes within a vacuum chamber, introducing monomeric starting material in the gas phase into the vacuum chamber and applying a radiofrequency of microwave discharge between the electrodes.

14. A sensor device according to claim 1, wherein said immobilized first molecules comprise biomolecules.

15. A sensor device according to claim 14, wherein said biomolecules comprise an antigen, hormone, polynucleotide strand, avidin, enzyme or carbohydrate.

16. A sensor device according to claim 14, wherein said second molecules comprise an antibody, hormone receptor, complementary strand, biotin, substrate, or lectin.

17. A sensor device according to claim 1, wherein said first molecules are immobilized upon said layer of diamond-like carbon by being covalently bound thereto.

18. A sensor device according to claim 1, wherein said layer of diamond-like carbon contains amino groups and said first molecules are covalently bound to said amino groups.

19. A sensor device according to claim 1, wherein said layer of diamond-like carbon contains carboxylate groups and said first molecules are covalently bound to said carboxylate groups.

* * * * *